(12) United States Patent
Härter et al.

(10) Patent No.: US 6,939,989 B2
(45) Date of Patent: Sep. 6, 2005

(54) SIDE-CHAIN HALOGENATED AMINO DICARBOXYLIC ACID DERIVATIVES AS MEDICAMENTS FOR TREATING CARDIOVASCULAR DISEASES

(75) Inventors: Michael Härter, Leverkusen (DE); Michael Hahn, Langenfeld (DE); Claudia Hirth-Dietrich, Wuppertal (DE); Andreas Knorr, Erkrath (DE); Elke Stahl, Bergisch Gladbach (DE); Johannes-Peter Stasch, Solingen (DE); Frank Wunder, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/469,178

(22) PCT Filed: Feb. 22, 2002

(86) PCT No.: PCT/EP02/01895

§ 371 (c)(1),
(2), (4) Date: Aug. 26, 2003

(87) PCT Pub. No.: WO02/070461

PCT Pub. Date: Sep. 12, 2002

(65) Prior Publication Data

US 2004/0082658 A1 Apr. 29, 2004

(30) Foreign Application Priority Data

Mar. 1, 2001 (DE) .......................................... 101 09 861

(51) Int. Cl.$^7$ ............................................... C07C 63/00
(52) U.S. Cl. ..................... 562/405; 562/433; 562/442; 562/443; 514/579
(58) Field of Search ................. 562/405, 433, 562/442, 443; 514/579

(56) References Cited

U.S. PATENT DOCUMENTS

| | | | |
|---|---|---|---|
| 6,166,027 A | 12/2000 | Straub et al. ................ | 514/269 |
| 6,180,656 B1 | 1/2001 | Furstner et al. ............. | 514/406 |
| 6,387,940 B1 | 5/2002 | Straub et al. ................ | 514/403 |
| 6,451,805 B1 | 9/2002 | Straub et al. ................ | 514/269 |

FOREIGN PATENT DOCUMENTS

| | | | | |
|---|---|---|---|---|
| DE | 19943635 A1 | * | 3/2001 | |
| EP | 0341551 | * | 11/1989 | |
| EP | 0345068 | | 12/1989 | ....... C07C/103/183 |
| WO | 9816223 | | 4/1989 | ......... A61K/31/415 |
| WO | 9300359 | | 7/1993 | ............. C07C/7/08 |
| WO | 9816507 | | 4/1998 | |
| WO | 9823619 | | 6/1998 | ......... C07C/487/04 |
| WO | 0019780 | | 6/2000 | |

OTHER PUBLICATIONS

Ko et al., YC–1, a Novel Activator of Platelet Guanylate Cyclase, Blood, 84, 4226–4233 (1994).
Mulsch, et al., Effect of YC–1, an NO–independent, Superoxide–Sensitive Stimulator of Soluble Guanylyl Cyclase, on Smooth Muscle Responsiveness to Nitrovasodilators, Brit. J. Pharm. 120, 681–689 (1997).
Glass et al., Stimulation of Human Platelet Guanylate Cyclase by Fatty Acids, J. Biol. Chem., 252, 1279–1285 (1977).
Pettibone et al., A Structurally Novel Stimulator of Guanylate Cyclase with Long–lasting Hypotensive Activity in the Dog, European J. Pharm. 116, 307–312 (1985).
Yu et al., Vasorelaxant Effect of Isoliquiritigenin, a Novel Soluble Guanylate Cyclase Activator, in Rat Aorta, Brit. J. Pharm. 114, 1587–1594 (1995).
Gerzer, et al, Soluble Guanylate Cyclase Purified From Bovine Lung Contains Heme and Copper, FEBS letters, 132, 71–74 (1981).
Hoenicka, et al. Purified Soluble Guanylyl Cyclase expressed in Baculovirus/Sf9 system: stimluation by Yc–1, nitric oxide, and carbon monoxide J. Mol. Med., 77, 14–23, (1999).
Ignarro, Louis J., Regulation of Cytosolic Guanylyl Cyclase By Porphyrins and Metallopophyrins, Advances in Pharmacol., 26, 35–65 (1994).
Pinzani, Massino. M.D.; Biology of Hepaic Stellate Cells and Their Possible Relevance in the Pathogenesis of Portal Hypertension in Cirrhosis, Seminars in Liver Disease, 19 397–410 (1999).
Müisch, et al., Potentiation of Vascular Responses to NO–Donors by an NO–independent Activation of Soluble Guanylyl Cyclase, Naunyn Schmiedebergs Arch. Pharmacol. 355, R47.

* cited by examiner

*Primary Examiner*—Cecilia J. Tsang
*Assistant Examiner*—Hector M. Reyes

(57) ABSTRACT

Compounds of the general formula (I)

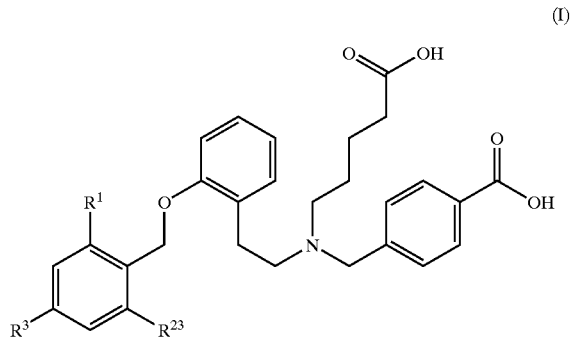

wherein $R^1$ represents halogen, $R^2$ represent H or halogen, and $R^3$ represents $C_{3-8}$-cycloalkyl, $C_{3-8}$-cycloalkenyl, or optionally substituted phenyl, pharmaceutical compositions containing such material, and methods of using such materials in the treatment of various diseases are disclosed and claimed.

8 Claims, No Drawings

SIDE-CHAIN HALOGENATED AMINO DICARBOXYLIC ACID DERIVATIVES AS MEDICAMENTS FOR TREATING CARDIOVASCULAR DISEASES

The present invention relates to novel side-chain-halogenated aminocarboxylic acid derivatives which stimulate soluble guanylate cyclase also via a novel mechanism of action which takes place without involvement of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory center. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in the neuronal signal transmission, and in disorders caused by an impairment of the aforementioned processes. Under pathophysiological conditions, the NO/cGMP system may be suppressed, which may lead for example to high blood pressure, platelet activation, increased cell proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected. Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmcol. 116 (1985), 307), isoliquiritigenin (Yu et al., Brit. J. Pharmacol. 114 (1995), 1587) and various substituted pyrazole derivatives (WO 98/16223, WO 98/16507 and WO 98/23619).

The stimulators of soluble guanylate cyclase described above stimulate the enzyme either directly via the heme group (carbon monoxide, nitrogen monoxide or diphenyliodonium hexafluorophosphate) by interaction with the central iron of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating action of NO or CO (for example YC-1, Hoenicka et al., J. Mol. Med. (1999) 14; or the pyrazole derivatives described in WO 98/16223, WO 98/16507 and WO 98/23619).

The stimulating action of isoliquiritigenin and of fatty acids, such as, for example, arachidonic acid, prostaglandin endoperoxides and fatty acid hydroperoxides, on soluble guanylate cyclase claimed in the literature could not be confirmed (cf., for example, Hoenicka et al., J. Mol. Med. 77 (1999), 14).

If the heme group is removed from soluble guanylate cyclase, the enzyme still has detectable catalytic basal activity, i.e. cGMP is still being formed. The residual catalytic basal activity of the heme-free enzyme cannot be stimulated by any of the known stimulators mentioned above.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, as a consequence of which the addition of protoporphyrin IX to soluble guanylate cyclase would be expected to result in the formation of a structure of the enzyme corresponding to heme-containing soluble guanylate cyclase stimulated by NO. This is also confirmed by the fact that the stimulating action of protoporphyrin IX is increased by the above-described NO-independent but heme-dependent stimulator YC-1 (Mülsch et al., Naunyn Schmiedebergs Arch. Pharmacol. 355, R47).

In contrast to the above-described compounds, known from the prior art as stimulators of soluble guanylate cyclase, the compounds according to the invention are capable of stimulating both the heme-containing and the heme-free form of soluble guanylate cyclase. Thus, in the case of these novel stimulators, stimulation of the enzyme is effected via a heme-independent path, and this is also confirmed by the fact that firstly the novel stimulators do not have any synergistic action with NO at the heme-containing enzyme and that secondly the action of these novel stimulators cannot be blocked by the heme-dependent inhibitor of soluble guanylate cyclase, i.e. 1H-1,2,4-oxadiazole-(4,3a)-quinoxalin-1-one (ODQ).

This is a novel therapeutic approach for treating cardiovascular disorders and other disorders accessible to therapy by influencing the cGMP signal pathway in organisms.

EP-A-0 345 068 describes, inter alia, the aminoalkanecarboxylic acid (1) as an intermediate in the synthesis of GABA antagonists:

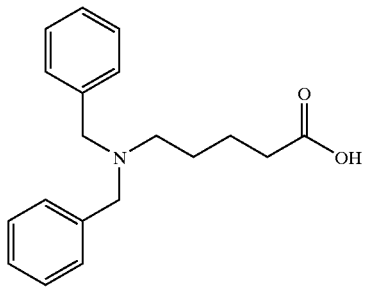

(1)

WO 93/00359 describes the aminoalkanecarboxylic acid (2) as an intermediate in peptide synthesis and its use as active compound for treating disorders of the central nervous system:

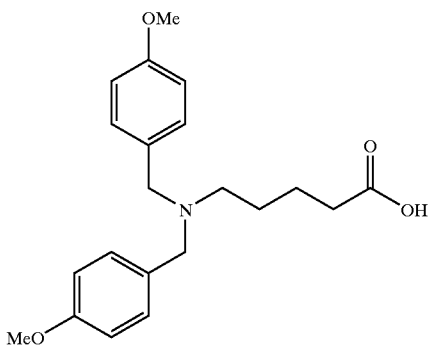

(2)

However, neither of these two publications describes that such aminoalkanecarboxylic acids may have a stimulating effect, independent of the heme group present in the enzyme, on soluble guanylate cyclase.

Substances having a structure similar to that of the compounds according to the invention are furthermore known from WO 01/19776, WO 01/19355, WO 01/19780 and WO 01/19778.

The present invention relates to compounds of the general formula (I)

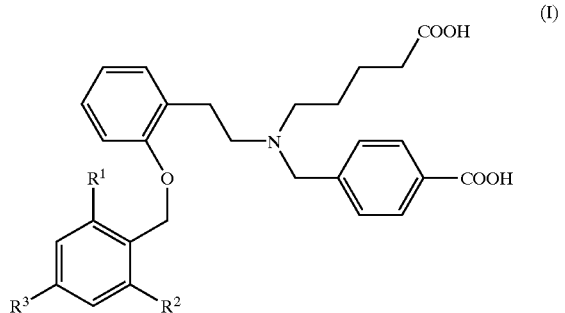

(I)

where
$R^1$ represents halogen;
$R^2$ represents H or halogen;
$R^3$ represents $C_{3-8}$-cycloalkyl, $C_{3-8}$-cycloalkenyl or phenyl, where the phenyl radical may additionally carry a substituent from the group consisting of halogen, $C_{1-6}$-alkyl, $C_{1-6}$-alkoxy, $CF_3$;
and their salts, isomers and hydrates.

According to a preferred embodiment, the present invention relates to compounds of the formula (I) in which
$R^1$ represents F or Cl;
$R^2$ represents H;
$R^3$ represents $C_{3-8}$-cycloalkyl, $C_{3-8}$-cycloalkenyl or phenyl, where the phenyl radical may additionally carry a substituent from the group consisting of F, Cl, Br, methyl, ethyl, n-propyl, i-propyl, n-butyl, i-butyl, t-butyl, methoxy, ethoxy, n-propoxy, i-propoxy, n-butyloxy, i-butyloxy, t-butyloxy, $CF_3$;
and their salts, isomers and hydrates.

According to a particularly preferred embodiment, the present invention relates to compounds of the formula (I) in which
$R^1$ represents F or Cl;
$R^2$ represents H;
$R^3$ represents cyclohexyl, 1-cyclohexenyl or phenyl, where the phenyl radical may additionally carry a substituent from the group consisting of F, Cl, t-butyl, OMe, $CF_3$;
and their salts, isomers and hydrates.

The compounds according to the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers), or not like image and mirror image (diastereomers). The invention relates both to the enantiomers or diastereomers and to their respective mixtures. The racemic forms, like the diastereomers, can be separated into the stereoisomerically uniform components in a known manner, for example by optical resolution or chromatographic separation. Double bonds present in the compounds according to the invention can be in the cis or trans configuration (Z or E form).

For the purposes of the present invention, the substituents are, unless defined otherwise, generally as defined below:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Cycloalkyl generally represents a cyclic hydrocarbon radical having 3 to 8 carbon atoms. Preference is given to cyclopropyl, cyclopentyl and cyclohexyl. Cyclopentyl, cyclohexyl, cycloheptyl and cyclooctyl may be mentioned by way of example.

Cycloalkenyl generally represents a cyclic hydrocarbon radical having 3 to 8 carbon atoms which additionally has a double bond in the ring. Preference is given to cyclopropenyl, cyclopentenyl and cyclohexenyl. Examples which may be mentioned are cyclopentenyl, cyclohexenyl, cycloheptenyl and cyclooctenyl.

Halogen, for the purposes of the invention, represents fluorine, chlorine, bromine and iodine.

The present invention furthermore relates to a process for preparing the compounds of the formula (I), characterized in that compounds of the formula (II)

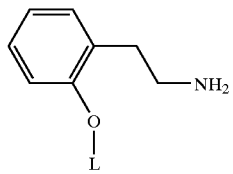

(II)

where

L represents methyl are reacted with a $C_{1-6}$-alkyl 4-formylbenzoate in an organic solvent, if appropriate with heating and simultaneous or subsequent addition of a reducing agent, to give compounds of the formula (III)

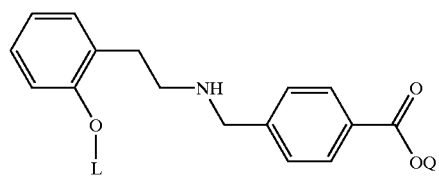

(III)

where

L is as defined above and Q represents a $C_{1-6}$-alkyl radical, subsequently—with prior ether cleavage to the free hydroxyl group—reacted with a $C_{1-6}$-alkyl ω-halovalerate in an organic solvent in the presence of a base with heating to give compounds of the formula (IV)

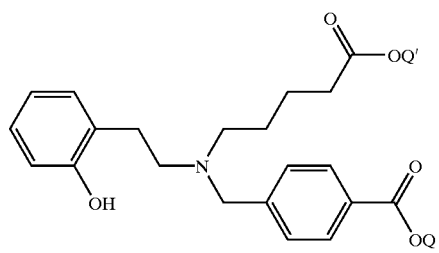

(IV)

where

Q is as defined above and Q' represents a $C_{1-6}$-alkyl radical, then reacted with a compound of the formula IV-A in an organic solvent in the presence of a base with heating

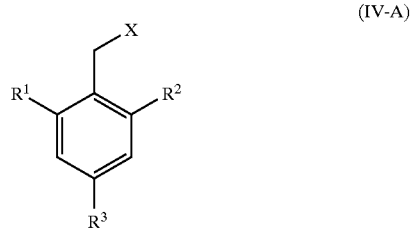

(IV-A)

where $R^1$, $R^2$ and $R^3$ are as defined above and X represents halogen to give compounds of the formula (V)

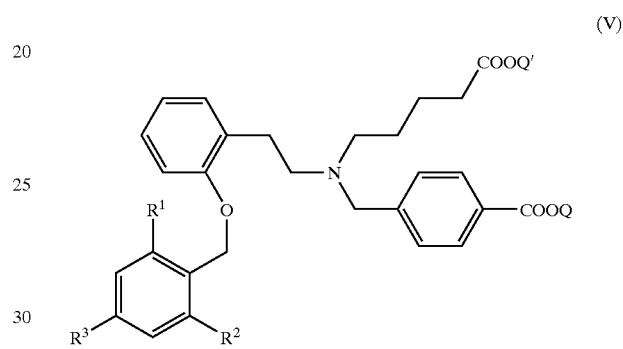

(V)

and the compounds of the formula (V) are then hydrolyzed under alkaline conditions to give the compounds of the formula (I).

The bases preferred for the processes according to the invention include basic compounds customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t-butoxide, or carbonates, such as sodium carbonate, cesium carbonate or potassium carbonate, or amides, such as sodium amide or lithium diisopropylamide, or organolithium compounds, such as phenyllithium, butyllithium or methyllithium, or sodium hexamethyldisilazane.

Solvents preferred for converting the compounds of the formula (II) into the compounds of the formula (III) are customary organic solvents which do not change under the reaction conditions. For the process according to the invention, preference is given to using ethers, such as diethyl ether, butyl methyl ether, dioxane, tetrahydrofuran, glycol dimethyl ether or diethylene glycol dimethyl ether, or hydrocarbons, such as benzene, toluene, xylene or petroleum ether, or alcohols, such as methanol or ethanol, or halogenated hydrocarbons, such as carbon tetrachloride, chloromethane or dichloromethane. It is, of course, also possible to use mixtures of the solvents mentioned above. Preference according to the invention is given to using toluene and/or methanol.

The compounds of the formula (II) are initially reacted with a $C_{1-6}$-alkyl 4-formylbenzoate to give a Schiff base which is then reduced with customary reducing agents, such as, for example, NaBH$_4$, H$_2$/Pd/C, etc., or reacted directly under the conditions of a reductive alkylation in the presence of a reducing agent, such as, for example, H$_2$/Pd/C, NaCNBH$_3$, NaH(OAc)$_3$ (cf. Patai, Ed., The Chemistry of the Carbon-Nitrogen Double Bond, pp. 276–293 and the literature cited therein). Depending on the nature of the starting material, the reaction may be carried out at room temperature or requires heating at from 50–110° C. for several hours to several days. The reaction can be carried out at atmospheric pressure, elevated or reduced pressure (for example in a range of from 0.5 to 5 bar). In general, the reaction is carried out under atmospheric pressure. $C_{1-6}$-Alkyl 4-formylbenzoates are commercially available, known from the literature, or can be synthesized analogously to processes known from the literature (cf., for example, J. Med. Chem. 1989, 32, 1277; Chem. Ber. 1938, 71, 335; Bull. Soc. Chim. Fr. 1996, 123, 679, WO96/11902; DE-2209128; Synthesis 1995, 1135; Bull. Chem. Soc. Jpn. 1985, 58, 2192, Synthesis 1983, 942; J. Am. Chem. Soc. 1992, 114, 8158).

Prior to the reaction of the corresponding compound of the formula (III) with the alkyl ω-halovalerate, the methoxy group present should be converted into the free hydroxyl group. This can be carried out in a known manner (cf. T. W. Greene, P. G. M. Wuts, Protective Groups in Organic Synthesis, second edition, New York, 1991). For example, the methyl group can be cleaved off with formation of the phenol using boron tribromide in methylene chloride at from −70 to 20° C., using trimethylsilyl iodide in chloroform at 25–50° C. or using sodium ethyl thiolate in DMF at 150° C. Preference according to the invention is given to the reaction with boron tribromide.

The conversion of the compounds of the formula (III) into the compounds of the formula (IV) can preferably be carried out in acetonitrile or butyronitrile, in each case in the presence of a base, such as sodium carbonate, Et$_3$N, DABCO, K$_2$CO$_3$, KOH, NaOH or NaH. In general, the reaction can be carried out in a temperature range of from −20° C. to +90° C., preferably of from 0° C. to +70° C. The reaction can be carried out under atmospheric pressure, elevated or reduced pressure (for example in a range of from 0.5 to 5 bar). In general, the reaction is carried out under atmospheric pressure. However, suitable solvents are, in principle, the solvents mentioned above for the conversion of the compounds of the formula (II) into the compounds of the formula (III). According to the invention, the alkyl ω-halovalerate used is, preferably, the corresponding ethyl ω-bromovalerate. Alkyl ω-halovalerates are commercially available, known from the literature or can be synthesized by processes known from the literature (cf., for example, B.J. Chem. Soc. 1958, 3065).

The compounds of the formula (IV) are then reacted with the compounds of the formula (IV-A). The reaction is a nucleophilic substitution of a leaving group X in the compound of the formula (IV-A) by the hydroxyl function of the compound of the formula (IV). Suitable leaving groups X are, for example: halogen, tosylate, mesylate, or a hydroxyl function activated by reagents such as diisopropyl azodicarboxylate/PPh$_3$ (Mitsonobu reaction). X is preferably halogen, particularly preferably Cl. This reaction can be carried out in one of the organic solvents mentioned above, preferably in acetonitrile, by reacting the compounds (IV) and (IV-A) in the presence of a base, such as sodium carbonate, NaH, Et$_3$N, DABCO, K$_2$CO$_3$, KOH, NaOH or preferably potassium carbonate. The reaction can generally be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out under atmospheric pressure.

The compounds of the formula (V) are then converted into the compounds of the formula (I) by hydrolysis of the ester functions to the free carboxyl groups, for example by adding aqueous solutions of strong acids, such as, for example, HCl or H$_2$SO$_4$, or strong bases, such as, for example, NaOH, KOH or LiOH. The reaction can be carried out in one of the organic solvents mentioned above, in water or in mixtures of organic solvents or in mixtures of organic solvents with water. Preference according to the invention is given, for example, to carrying out the reaction in a mixture of water and methanol or dioxane. The reaction can generally be carried out in a temperature range of from −20° C. to +90° C., preferably from 0° C. to +90° C. The reaction can be carried out under atmospheric pressure, elevated or reduced pressure (for example in a range of from 0.5 to 5 bar). In general, the reaction is carried out under atmospheric pressure.

The compounds of the formula (II) are commercially available or known from the literature.

The compounds of the formula (IV-A) are either commercially available, known from the literature or obtainable, for example, in the manner described below. Starting from 2,4-halobenzoic acids, which are commercially available or known from the literature, initially the corresponding alkyl 2,4-halobenzoates are prepared by esterification under customary conditions, for example using chlorotrimethylsilane in methanol, which are converted by reaction with a benzeneboronic acid derivative in the presence of a palladium compound and, if appropriate, a reducing agent and further additives in basic medium into the corresponding biphenyl compounds. Formally, the latter reaction is a reductive coupling as described, for example, in L. S. Hegedus, Organometallics in Synthesis, M. Schlosser, Ed., Wiley & Sons, 1994. The palladium compound used can be a palladium (II) compound, such as, for example, Cl$_2$Pd(PPh$_3$)$_2$ or Pd(OAc)$_2$ or a palladium(0) compound, such as, for example, Pd(PPh$_3$)$_4$ or Pd$_2$(dba)$_3$. If required, a reducing agent, such as, for example, triphenylphosphine, or other additives, such as, for example, Cu(I)Br, NBu$_4$NCl, LiCl or Ag$_3$PO$_4$, may additionally be added to the reaction mixture (cf. T Jeffery, Tetrahedron Lett. 1985, 26, 2667–2670; T. Jeffery, J. Chem. Soc., Chem. Commun. 1984, 1287–1289; S. Bräse, A. deMejiere in "Metal-catalyzied cross-coupling reactions", Ed. F. Diederich, P. J. Stang, Wiley-VCH, Weinheim 1998, 99–166). The reaction is carried out in the presence of a customary base, such as, for example, Na$_2$CO$_3$, NaOH or triethylamine. Suitable solvents are the organic solvents mentioned above, ethers, such as, for example, 1,2-dimethoxyethane, being particularly preferred. In general, the reaction can be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out under atmospheric pressure.

Benzeneboronic acids are commercially available, known from the literature or can be synthesized analogously to processes known from the literature (cf., for example, J. Chem.Soc.C 1966, 566, J.Org. Chem., 38, 1973, 4016).

The compounds of the formula (IV-A) can then be prepared by converting the carboxylic acid ester function by reduction to the corresponding alcohol function using, for example, LiAlH$_4$, and conversion of the alcohol function into the corresponding halide, for example the corresponding chloride, using a customary halogenating agent, such as, for example, thionyl chloride.

The compounds of the general formula (I) according to the invention show a valuable range of pharmacological effects which could not have been predicted.

The compounds of the general formula (I) according to the invention bring about vasorelaxation and an inhibition of platelet aggregation and lead to a reduction in blood pressure and an increase in the coronary blood flow. These effects are mediated by direct stimulation of soluble guanylate cyclase and an intracellular increase in cGMP.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenosis such as after thrombolysis therapies, percutaneous transluminal angioplasties (PTAs), percutaneous transluminal coronary angioplasties (PTCAs), bypass and for the treatment of arteriosclerosis, fibrotic disorders, such as fibrosis of the liver or pulmonary fibrosis, asthmatic disorders and diseases of the urogenital system such as, for example, prostate hypertrophy, erectile dysfunction, female sexual dysfunction and incontinence and also for the treatment of glaucoma.

The compounds of the general formula (I) described in the present invention are also active compounds suitable for controlling central nervous system diseases characterized by disturbances of the NO/cGMP system. They are suitable in particular for removing cognitive deficits, for improving learning and memory performances and for treating Alzheimer's disease. They are also suitable for treating disorders of the central nervous system such as states of anxiety, tension and depression, CNS-related sexual dysfunctions and sleep disturbances, and for controlling pathological disturbances of the intake of food, stimulants and addictive substances.

The active compounds are furthermore also suitable for regulating cerebral blood flow and thus represent effective agents for controlling migraine.

They are also suitable for the prophylaxis and control of the sequelae of cerebral infarction (apoplexia cerebri) such as stroke, cerebral ischemias and craniocerebral trauma. The compounds of the general formula (I) according to the invention can likewise be employed for controlling states of pain.

In addition, the compounds according to the invention have an anti-inflammatory effect and can therefore be employed as anti-inflammatory agents.

As a particular and surprising feature, the compounds of the present invention have an unexpectedly long duration of action.

Vasorelaxant Effect in vitro

Rabbits are anesthetized or killed by intravenous injection of thiopental sodium (about 50 mg/kg) and exsanguinated. The arteria saphena is removed and divided into rings 3 mm wide. The individual rings are in each case mounted on a pair of hooks of triangular shape, open at the ends and made of special wire (Remanium®) having a diameter of 0.3 mm. Under pretension, each ring is introduced into a 5 ml organ bath containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10; bovine serum albumin: 0.001%. The force of contraction is detected with Statham UC2 cells, amplified and digitized via A/D converters (DAS-1802 HC, Keithley Instruments, Munich) and recorded in parallel on chart recorders. Contractions are generated by adding phenylephrine.

After several (generally 4) control cycles, the substance to be investigated is added in each further run in increasing dosage, and the height of the contraction reached under the influence of the test substance is compared with the height of the contraction reached in the last preceding run. The concentration necessary to reduce the height of the control value by 50% ($IC_{50}$) is calculated from this. The standard application volume is 5 μl. The DMSO content in the bath solution corresponds to 0. 1%.

The results are shown in Table 1:

TABLE 1

| Vasorelaxant effect in vitro | |
|---|---|
| Example | $IC_{50}$ (nM) |
| 2 | 0.15 |
| 6 | 0.17 |
| 9 | 1.8 |
| 12 | 2 |

Stimulation of Recombinant Soluble Guanylate Cyclase (sGC) in vitro

The investigations of the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out according to the method described in detail in the following literature reference: M. Hoenicka, E. M. Becker, H. Apeler, T. Sirichoke, H. Schroeder, R. Gerzer and J.-P. Stasch: Purified soluble guanylyl cyclase expressed in a baculovirus/Sf9 system: stimulation by YC-1, nitric oxide, and carbon oxide. J. Mol. Med. 77 (1999): 14–23.

The heme-free guanylate cyclase was obtained by adding Tween 20 to the sample buffer (final concentration 0.5%).

Activation of sGC by a test substance is stated as n-fold stimulation of basal activity. The results are shown in Table 2:

TABLE 2

Stimulation of recombinant soluble guanylate cyclase (sGC) in vitro

| | Stimulation (n-fold) Heme-containing sGC | | | | | Heme-free sGC | |
|---|---|---|---|---|---|---|---|
| Ex. 6 Concentration (μM) | basal | + DEA/NO (0.001 μM) | + DEA/NO (0.01 μM) | + DEA/NO (0.1 μM) | + ODQ (10 μM) | basal | + ODQ (10μM) |
| 0 | 1 | 5 | 30 | 124 | — | 1 | — |
| 0.001 | 2 | 6 | 32 | 127 | 35 | 10 | 25 |
| 0.01 | 9 | 13 | 39 | 134 | 95 | 55 | 61 |
| 0.1 | 18 | 25 | 52 | 157 | 147 | 81 | 79 |
| 1.0 | 23 | 30 | 53 | 151 | 150 | 83 | 83 |
| 10 | 25 | 30 | 67 | 174 | 159 | 84 | 83 |

Table 2 shows that stimulation both of the heme-containing and the heme-free enzyme is achieved. Furthermore, a combination of sGC stimulator and 2-(N,N-diethylamino)diazenolate 2-oxide (DEA/NO), an NO donor, shows no synergistic effect, i.e. the action of DEA/NO is not potentiated as would be expected for sGC stimulators acting via a heme-dependent mechanism. In addition, the action of the sGC stimulator according to the invention is not blocked by the heme-dependent inhibitor of soluble guanylate cyclase ODQ. Thus, the results from Table 2 confirm the novel mechanism of action of the stimulators according to the invention of soluble guanylate cyclase.

Investigation of the Antifibrotic Action of the Substances in vivo

Method

The antifibrotic action of the substances was investigated using the model of the porcine serum-induced rat liver fibrosis. Treatment with heterologous serum, for example porcine serum in rats, is a method frequently used in the literature for inducing fibrosis of the liver with subsequent cirrhosis which, in contrast to other models, causes only minimal damage and inflammation of the parenchyma cells of the liver (Bhunchet, E. and Wake, K. (1992): Role of mesenchymal cell populations in porcine serum-induced rat liver fibrosis. Hepatology 16: 1452–1473). Female Sprague Dawley rats were treated 2×per week with 0.5 ml/animal of sterile porcine serum (Sigma) i.p., control animals were treated with sterile physiological saline (2×per week 0.5 ml/animal i.p.). The treatment with test substance (1×per day in 5 ml/kg of p.o. solvent comprising 20% Cremophor, 10% Transcutol and 70% $H_2O$) was carried out in parallel to the treatment with porcine serum. After seven weeks of treatment, the animals were killed and the livers were removed in order to quantify the collagen content.

For the histological examination of the liver tissue, standardized transverse tissue cylinders (about 10×2 mm) were punched out of the right anterior lobe of the liver. For the detection of scar collagen caused by liver fibrosis, frozen sections were stained with 0.1% strength Pikrosirius Red solution.

Fast Green was used as counterstain to enhance contrasts. In each section, the extent of liver fibrosis was determined as a percentage of the area stained by Pikrosirius Red of the total area measured. The parameters of the video microscopic stain detection were standardized and kept constant for the entire experiment. 64 fields of a standardized grid of 31 $mm^2$ were measured using a final amplification of 100. For semiautomatic morphometry, a Leica Quantimed 500MC (Leica Germany) was used.

To determine OH-proline according to Prockop and Udenfried (Prockop, D. J. and Udenfried, S. A. (1960): A specific method for the analysis of hydroxyproline in tissues and urine. Anal. Biochem. 1: 228–239), in each case 50–100 mg of liver tissue were dried and boiled with 6N HCl for about 17 hours. The acid was evaporated in a vacuum drying cabinet and the residue was then dissolved in 5 ml of distilled water and filtered. 200 µl of the filtered solution were incubated at room temperature with 200 µl of ethanol and 200 µl of oxidation solution (7% strength aqueous chloramine T hydrate solution, diluted 1:4 with acetate/citrate buffer pH 6.0) for 25 min. 400 µl of Ehrlich's reagent (12 g of 4-dimethylaminobenzaldehyde in 20 ml of ethanol+ 2.74 ml of concentrated sulfuric acid in 20 ml of ethanol) were then added. After 3 hours of incubation at 35° C., absorption at 573 nm was measured. Aqueous OH-proline solutions (Sigma) were used for the calibration curve. The OH-proline content of the liver samples was calculated in mg per g of liver dry weight.

Results

The OH-proline values agree very well with the results of the morphometric fibrosis measurement: without simultaneous administration of substance, the porcine serum treatment results in a pronounced accumulation of collagen in the liver. The formation of these collagen deposits is reduced by treatment with the substances; in Example 6 doses of just 0.03 mg/kg and 0.1 mg/kg p.o.o.d. produce a significant reduction of about a half.

The present invention includes pharmaceutical preparations which, in addition to non-toxic, inert, pharmaceutically acceptable carriers, comprises the compounds according to the invention, in particular the compounds of the general formula (I), and processes for preparing these preparations.

The active compound, if appropriate in one or more of the carriers listed above, can also be present in microencapsulated form.

The therapeutically effective compounds, in particular the compounds of the general formula (I), should be present in the pharmaceutical preparations detailed above in a concentration of about 0.1 to 99.5, preferably of about 0.5 to 95, % by weight of the complete mixture.

The pharmaceutical preparations detailed above may, apart from the compounds according to the invention, in particular the compounds of the general formula (I), also contain other active pharmaceutical ingredients.

It has generally proved to be advantageous both in human and in veterinary medicine to administer the active compound(s) according to the invention in total amounts of about 0.5 to about 500, preferably 5 to 100, mg/kg of body weight every 24 hours, where appropriate in the form of a plurality of single doses, to achieve the desired results. A single dose contains the active compound(s) according to the invention preferably in amounts of about 1 to about 80, in particular 3 to 30, mg/kg of body weight.

Below, the present invention is illustrated in more detail using non-limiting preferred examples. Unless indicated otherwise, all quantities refer to percent by weight.

EXAMPLES

Abbreviations:

| RT: | room temperature |
| --- | --- |
| EA: | ethyl acetate |
| BABA: | n-butyl acetate/n-butanol/glacial acetic acid/phosphate buffer | pH 6
(50:9:25.15; org. phase)

Mobile Phases for Thin-layer Chromatography:

| T1 E1: | toluene-ethyl acetate (1:1) |
| --- | --- |
| T1 EtOH1: | toluene-methanol (1:1) |
| C1 E1: | cyclohexane-ethyl acetate (1:1) |
| C1 E2: | cyclohexane-ethyl acetate (1:2) |

Starting Materials

Ex. I methyl 4-({[2-(2-methoxyphenyl)ethyl]amino}methyl)benzoate

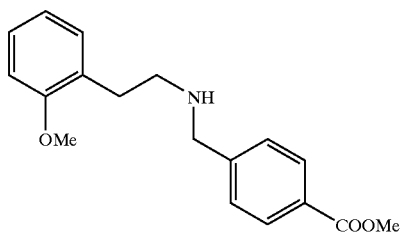

A solution of 92.08 g (0.597 mol) of 2-methoxyphenethylamine and 98.0 g (0.597 mol) of methyl 4-formylbenzoate in 2 l of ethanol is heated at reflux for 2 hours. The solvent is then removed under reduced pressure and the resulting residue is dissolved in 1 l of methanol. In total, 46.14 g of solid NaBH$_4$ are added a little at a time. After two hours of stirring at room temperature, the mixture is poured into water and extracted with ethyl acetate. The organic extract is washed with saturated sodium chloride solution and dried over Na$_2$SO$_4$. After filtration, the solvent is removed under reduced pressure. This gives 167.7 g (0.559 mol, 77% yield) of a colorless oil which is used without further purification for the next step.

$^1$H NMR (200 MHz, DMSO-d$_6$, δ/ppm): 7.90 (2H, d), 7.45 (2H, d), 7.17 (1H, t), 7.12 (1H, d), 6.92 (1H, d), 6.83 (1H, t), 3.83 (3H, s), 3.78 (2H, s), 3.73 (3H, s), 2.75–2.63 (4H, m). MS (DCI, NH$_3$): 300 (M+H$^+$).

Ex. II methyl 4-({[2-(2-hydroxyphenyl)ethyl]amino}methyl)benzoate hydrobromide

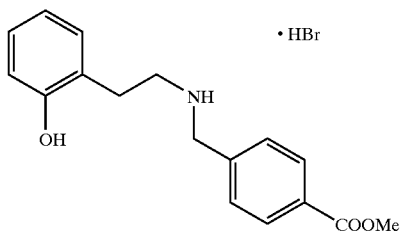

At 0° C., 661.4 ml (0.66 mol) of a 1-molar solution of boron tribromide in dichloromethane are added to a solution of 60.0 g (0.2 mol) of methyl 4-({[2-(2-methoxyphenyl)ethyl]amino}methyl) benzoate from Ex. 1 in 200 ml of dichloromethane. The mixture is stirred at 0° C. for one hour. 300 ml of methanol are then added, and the mixture is heated at reflux for 18 hours. On cooling, the product precipitates out and is filtered off. Further product is obtained by concentrating the mother liquor. The collected product fractions are washed with ether. This gives 45.04 g (0.16 mol, 56% yield) of a white crystalline solid.

R$_f$ (dichloromethane/methanol 10:1): 0.54. $^1$H NMR (300 MHz, DMSO-d$_6$, δ/ppm): 9.58 (1H, broad), 9.02 (2H, broad), 8.03 (2H, d), 7.68 (2H, d), 7.09 (1H, d), 7.07 (1H, t), 6.82 (1H, d), 6.77 (1H, t), 4.29 (2H, s), 3.89 (3H, s), 3.18–3.10 (2H, m), 2.94–2.88 (2H, m). MS (ESI): 286 (M+H$^+$).

Ex. III methyl 4-{[[2-(2-hydroxyphenyl)ethyl](5-methoxy-5-oxopentyl)-amino]methyl}benzoate

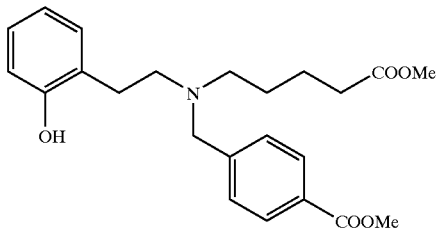

3.0 g (8.19 mmol) of methyl 4-({[2-(2-hydroxyphenyl)ethyl]amino}methyl)benzoate hydrobromide from Ex. II, 1.3 ml (9.83 mmol) of ethyl 5-bromovalerate and 1.74 g (16.38 mmol) of anhydrous sodium carbonate in 20 ml of acetonitrile are heated at reflux for three days. The mixture is then evaporated to dryness and the residue is taken up in ethyl acetate and washed with water and saturated sodium chloride solution. After drying over Na$_2$SO$_4$, the mixture is filtered and concentrated by evaporation. The product is purified by flash chromatography (silica gel, cyclohexane/ethyl acetate 7:3). This gives 2.2 g (5.51 mmol, 67% yield) of a pale yellow oil.

R$_f$ (cyclohexane/ethyl acetate 1:1): 0.28. $^1$H NMR (300 MHz, DMSO-d$_6$, δ/ppm): 9.57 (1H, s broad), 7.89 (2H, d), 7.43 (2H, d), 6.99 (1H, d), 6.98 (1H, t), 6.72 (1H, d), 6.67 (1H, t), 3.83 (3H, s), 3.69 (2H, s), 3.57 (3H, s), 2.71–2.66 (2H, m), 2.62–2.55 (2H, m), 2.45 (2H, t), 2.23 (2H, t), 1.51–1.40 (4H, m). MS (DCI, NH$_3$): 400 (M+H+), 252.

Ex. IV methyl 4-bromo-2-fluorobenzoate

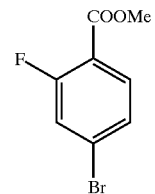

0.46 ml (3.65 mmol) of chlorotrimethylsilane is added to a solution of 8 g (36.53 mmol) of 4-bromo-2-fluorobenzoic acid in 44 ml of methanol, and the mixture is heated at reflux for 12 h. The mixture is then concentrated by evaporation, taken up in cyclohexane and filtered through silica gel. This gives 4.487 g (19.25 mmol, 52% yield) of a white solid.

R$_f$ (cyclohexane/ethyl acetate 2:1): 0.5. $^1$H NMR (200 MHz, DMSO-d$_6$, δ/ppm): 7.84 (1H, t), 7.75 (1H, dd), 7.58 (1H, dd), 3.88 (3H, s). MS (EI): 232 (M$^+$).

Ex. V methyl 3-fluoro-4'-methoxy-1,1'-biphenyl-4-carboxylate

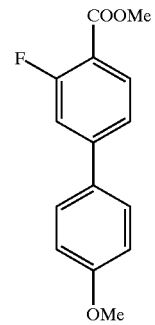

1.45 g (6.22 mmol) of methyl 4-bromo-2-fluorobenzoate from Ex. IV is dissolved in 15 ml of 1,2-dimethoxyethane, and 1.13 g (7.47 mmol) of 4-methoxybenzeneboronic acid, 80 mg (0.11 mmol) of bis(triphenylphosphine)palladium(II) chloride and 7 ml of a 2-molar solution of Na$_2$CO$_3$ in water are added under argon. The reaction mixture is then stirred under reflux for 12 h. The mixture is then cooled and filtered through 10 g of Extrelute, the filter cake is washed with dichloromethane and the filtrate is concentrated using a rotary evaporator. The resulting product is purified by flash chromatography (silica gel, cyclohexane/ethyl acetate 2:1). This gives 1.362 g (5.23 mmol, 84% yield) of a white solid.

$R_f$ (cyclohexane/ethyl acetate 2:1): 0.44. $^1$H NMR (200 MHz, DMSO-d$_6$, δ/ppm): 7.96 (1H, t), 7.80–7.62 (2H, m), 7.49–7.28 (3H, m), 7.02 (1H, dd); 3.89 (3H, s), 3.82 (3H, s). MS (EI): 260 (M$^+$).

Ex. VI
(3-fluoro-4'-methoxy-1,1'-biphenyl-4-yl)-methanol

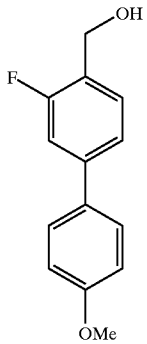

At 0° C., a solution of 1.36 g (5.23 mmol) of methyl 3-fluoro-4'-methoxy-1,1'-biphenyl-4-carboxylate from Ex. V in 10 ml of anhydrous TMF is added dropwise to 3.14 ml (3.14 mmol) of a 1-molar solution of LiAlH$_4$ in anhydrous THF. The mixture is initially stirred at 0° C. for 2 h. 10 ml of a sat. solution of NH$_4$Cl are then added carefully, the mixture is diluted with ethyl acetate and the organic phase is separated off. The organic phase is washed successively with water and saturated sodium chloride solution, dried over anhydrous sodium sulfate and, after filtration, freed from the solvent. The resulting crude product is purified by flash chromatography (silica gel, cyclohexane/ethyl acetate 5:1). This gives 914 mg (3.94 mmol, 73% yield) of (3-fluoro-4'-methoxy-1,1'-biphenyl-4-yl) methanol.

$R_f$ (cyclohexane/ethyl acetate 2:1): 0.29. $^1$H NMR (300 MHz, DMSO-d$_6$, δ/ppm): 7.58–7.45 (3H, m), 7.39 (1H, t), 7.29–7.20 (2H, m), 6.95 (1H, dd), 5.30 (1H, t), 4.58 (2H, d), 3.83 (3H, s). MS (EI): 232 (M$^+$).

Ex. VII
4-(chloromethyl)-3-fluoro-4'-methoxy-1,1'-biphenyl

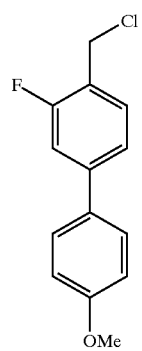

0.54 ml (7.45 mmol) of thionyl chloride, dissolved in 2 ml of chloroform, is added slowly to a solution of 864 mg (3.72 mmol) of (3-fluoro-4'-methoxy-1,1'-biphenyl-4-yl) methanol from Ex. VI in 3 ml of chloroform, and the mixture is stirred at room temperature for 12 h. The mixture is then concentrated by evaporation, taken up in ethyl acetate and washed with water and, twice, with a sat. solution of NaHCO$_3$. After drying over MgSO$_4$, filtration and concentration, the product is purified by flash chromatography (silica gel cyclohexane/ethyl acetate 100:1). This gives 511 mg (2.04 mmol, 55% yield) of a colorless oil.

$R_f$ (cyclohexane/ethyl acetate 2:1): 0.52. $^1$H NMR (200 MHz, DMSO-d$_6$, δ/ppm): 7.68–7.52 (3H, m), 7.46–7.21 (3H, m), 6.99 (1H, dd), 4.86 (2H, s), 3.86 (3H, s). MS (EI): 250 (M$^+$).

Ex. VIII
methyl 4-{[(2-{2-[(3-fluoro-4'-methoxy-1,1'-biphonyl-4-yl)methoxy]-phenyl}ethyl)(5-ethoxy-5-oxopentyl)amino]methyl}benzoate

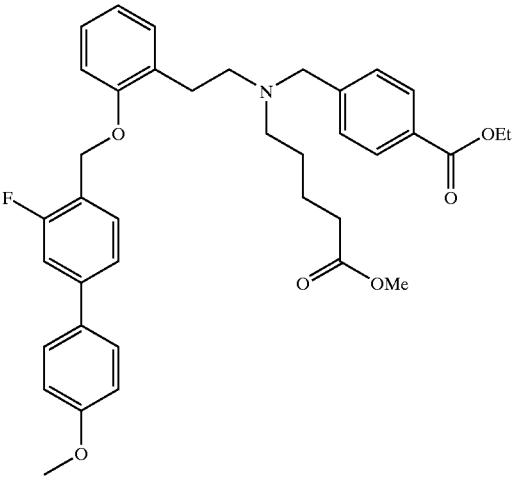

702 mg (1.7 mmol) of methyl 4-{[[2-(2-hydroxyphenyl)ethyl](5-ethoxy-5-oxopentyl)amino]methyl}benzoate from Ex. III and 352 mg (2.55 mol) of anhydrous potassium carbonate are added to a solution of 511 mg (2.04 mmol) of 4-(chloromethyl)-3-fluoro-4'-methoxy-1,1'-biphenyl from Ex. VII in 7 ml of dry acetonitrile, and the mixture is heated at reflux for 12 hours. The mixture is then evaporated to dryness using a rotary evaporator. The resulting crude product is purified by flash chromatography (cyclohexane/ethyl acetate 6:1). This gives 1.018 g (1.62 mmol, 94% yield) of a solid.

$R_f$ (cyclohexane/ethyl acetate 2:1): 0.30. $^1$H NMR (300 MHz, DMSO-d$_6$, δ/ppm): 7.80 (2H, d), 7.56 (1H, d), 7.51–7.48 (2H, m), 7.41–7.05 (8H, m), 6.98 (1H, dd), 6.89 (1H, t), 5.12 (2H, s), 3.99 (2H, q), 3.86 (3H, s), 3.81 (3H, s), 3.59 (2H, s), 2.78–2.68 (2H, m), 2.63–2.53 (2H, m), 2.39 (2H, t), 2.11 (2H, t), 1.48–1.27 (4H, m), 1.10 (3H, t). MS (ESI): 628 (M+H$^+$).

SYNTHESIS EXAMPLES

Ex. 1
4-{[(4-carboxybutyl)(2-{2-[(3-fluoro-4'-methoxy-1,1'-biphenyl-4-yl)methoxy]phenyl}ethyl)amino]methyl}benzoic acid

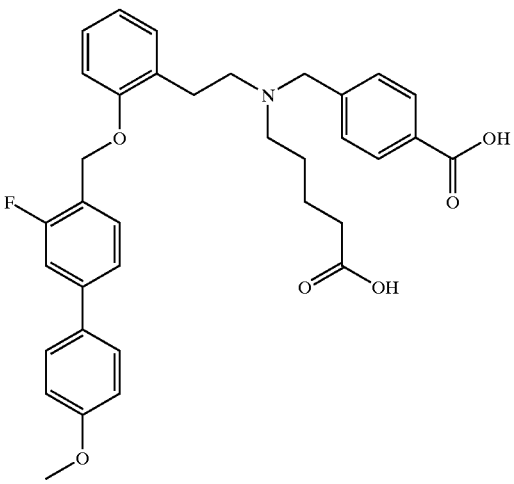

0.46 ml of a 45% strength solution of NaOH in water is added to a solution of 222 mg (0.37 mmol) of methyl 4-{[(2-{2-[(3-fluoro-4'-methoxy-1,1'-biphenyl-4-yl)methoxy]phenyl}ethyl)(5-ethoxy-5-oxopentyl)amino]methyl}benzoate from Ex. VIII in 10 ml of dioxane and 5 ml of water, and the mixture is stirred at 90° C. for 2 hours. After cooling, the dioxane is removed and the aqueous phase is adjusted to pH4 to 5 using 1-molar hydrochloric acid. This results in the precipitation of the product, which is filtered off, washed with water and dried. This gives 738 mg (1.26 mmol, 81% yield) of a white solid.

$R_f$(dichloromethane/methanol 7:3): 0.25. $^1$H NMR (200 MHz, DMSO-d$_6$, δ/ppm): 12.99–12.0 (2H, broad s), 7.82 (2H, d), 7.63 (2H, d) 7.54–7.41 (3H, m), 7.31 (2H, d), 7.24–7.03 (3H, m), 7.01 (2H, d), 6.89 (1H, t), 5.09 (2H, s), 3.80 (3H, s), 3.59 (2H, broad s), 2.78–2.65 (2H, m), 2.63–2.53 (2H, m), 2.45–2.31 (2H, m), 2.09 (2H, t), 1.47–1.30 (4H, m). MS (ESI): 586 (M+H$^+$).

The following compounds were obtained in an analogous manner:

| Ex. | Formula | $^1$H NMR δ [ppm] (DMSO-d$_6$) |
|---|---|---|
| 2 (from 4-t-butylbenzene-boronic acid) | | 12.32(2H, broad), 7.84 (2H, d), 7.61 (2H, d), 7.58–7.44 (5H, m), 7.41–7.28 (2H, m), 7.25–7.05 (3H, m), 6.89 (1H, t), 5.12 (2H, s), 3.80–3.51 (2H, m), 2.81–2.57 (4H, m), 2.55–2.38 (2H + DMSO, m), 2.10 (2H, t), 1.49–1.38 (4H, m), 1.31 (9H, s). (300MHz) |
| 3 (from 4-trifluoro-methyl-benzene-boronic acid) | | 12.5 (2H, broad), 8.01–7.87 (4H, m), 7.80 (2H, d), 7.73–7.54 (5H, m), 7.32–7.09 (3H, m), 6.94 (1H, t), 5.20 (2H, s), 4.48–4.30 (2H, m), 3.20–2.90 (4H, m), 2.52–2.42 (2H + DMSO, m), 2.14 (2H, t), 1.75–1.57 (2H, m), 1.48–1.32 (2H, m). (300MHz) |

-continued

| Ex. | Formula | $^1$H NMR δ [ppm] (DMSO-$d_6$) |
|---|---|---|
| 4 (from 4-bromo-2-chlorobenzoic acid and 4-methoxy-benzene-boronic acid) | 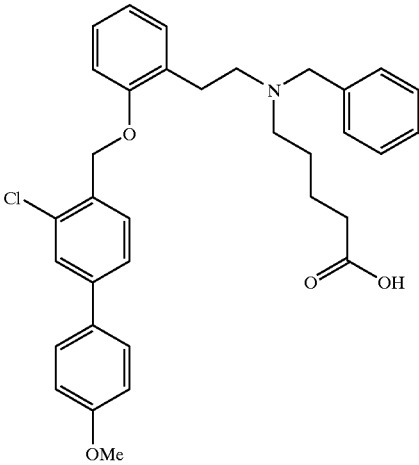 | 12.45 (2H, broad s), 7.89–7.77 (2H, m), 7.74 (1H, s), 7.63 (2H, d), 7.59 (2H, s), 7.42–7.29 (2H, m), 7.17 (2H, t), 7.10–6.97 (3H, m), 6.89 (1H, t), 5.12 (2H, s), 3.82 (3H, s), 3.70–3.51 (2H, m), 2.91–2.32 (6H + DMSO, m), 2.09 (2H, t), 1.51–1.39 (4H, m). (200MHz) |
| 5 (from 4-bromo-2-chloro-benzoic acid and 4-fluoro-benzene-boronic acid) | 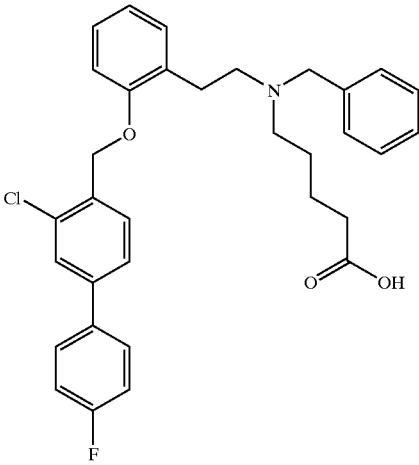 | 12.7–12.1 (2H, broad), 7.91–7.89 (2H, m), 7.88 (1H, d), 7.58 (2H, dd), 7.47 (2H, d), 7.42–6.99 (6H, m), 7.02 (1H, d), 6.89 (1H, t), 5.07 (2H, s), 3.68–3.49 (2H, broad), 2.90–2.30 (6H + DMSO, m), 2.12 (2H, m), 1.52–1.30 (4H, m). (200MHz) |
| 6 (from 4-bromo-2-chloro-benzoic acid and 4-triflouro-methyl-benzene-boronic acid) | 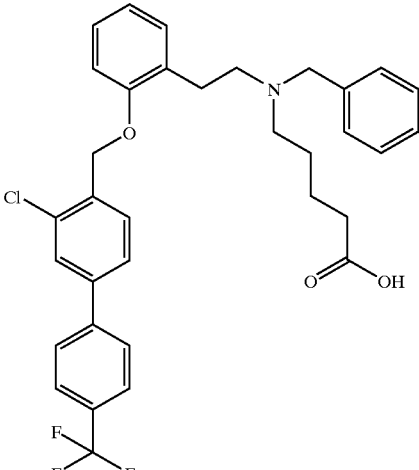 | 12.40 (2H, broad), 8.01–7.52 (11H, m), 7.38–7.03 (3H, m), 7.02–6.85 (1H, m), 5.20 (2H, s), 4.39 (2H, s), 3.30–2.89 (6H, m), 2.21–2.02 (2H, m), 1.74–1.52 (2H, m), 1.48–1.28 (2H, m). (300MHz) |

| Ex. | Formula | $^1$H NMR δ [ppm] (DMSO-d$_6$) |
|---|---|---|
| 7 (from 4-chloro-benzene-boronic acid) | 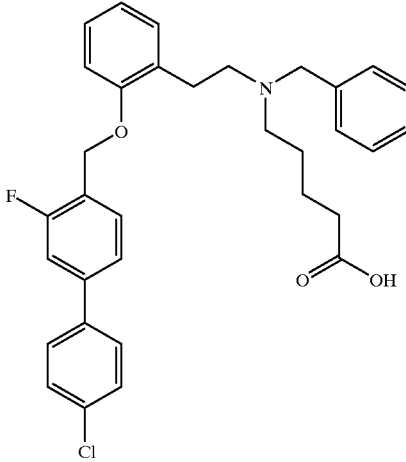 | 12.2 (2H, broad), 7.99–7.78 (2H, m), 7.71 (2H, d), 7.62–7.43 (6H, m), 7.40–7.01 (4H, m), 6.90 (1H, t), 5.14 (2H, s), of 4.60–1.28 (14H, m) therein 2.18–2.01 (2H, m), 1.49–1.28 (2H, m). (300MHz) |
| 8 (from 1-cyclohex-1-eneboronic acid) | 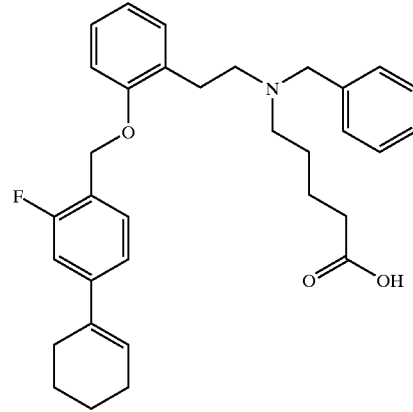 | 12.4 (2H, broad), 7.81 (2H, d), 7.44–6.99 (8H, m), 6.85 (1H, t), 6.24 (1H, t), 5.03 (2H, s), 3.57 (2H, s), 2.78–2.62 (2H, m), 2.61–2.45 (2H + DMSO, m), 2.44–2.26 (4H, m), 2.25–2.00 (4H, m), 1.79–1.50 (4H, m), 1.48–1.28 (4H, m). (200MHz) |
| 9 (from 4-bromo-2-chloro-benzoic acid and 1-cyclohex-1-eneboronic acid) | 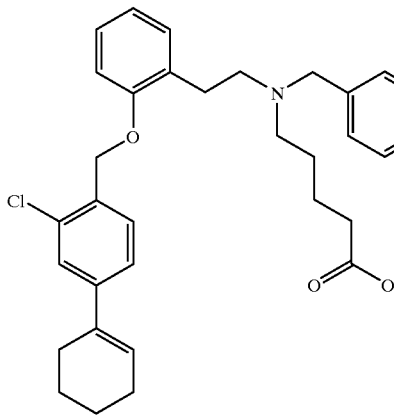 | 12.3 (1H, broad), 10.2 (1H, broad), 7.98 (2H, d), 7.72–7.57 (2H, m), 7.54–7.42 (2H, m), 7.36 (1H, d), 7.31–7.17 (2H, m), 7.10 (1H, d), 6.95(1H, t), 6.24 (1H, t), 5.12(2H, s), 4.38 (2H, s), 3.32–2.89 (5H, m), 2.39–2.26 (2H, m), 2.25–2.04 (5H, m), 1.81–1.48 (6H, m), 1.47–1.27(2H, m). (200MHz) |

| Ex. | Formula | ¹H NMR δ [ppm] (DMSO-d₆) |
|---|---|---|
| 10 (from 4-bromo-2-chloro-benzoic acid and 4-t-butylbenzene boronic acid) | | 12.4 (2H, broad), 7.89–7.78 (2H, m), 7.77 (1H, s) 7.64–7.53 (4H, m), 7.49 (2H, d), 7.44–7.28 (2H, m), 7.27–7.11 (2H, m), 7.08 (1H, d), 6.91 (1H, t), 5.13 (2H, s), 3.75–3.52 (2H, broad), 2.90–2.60 (6H, broad), 2.11 (2H, t), 1.49–1.38 (4H, m), 1.33 (9H, s). (300MHz) |
| 11 (from 1-cyclohexane-boronic acid) | | 12.4 (2H, broad), 7.99–7.74 (2H, broad), 7.43–6.80 (9H, m), 5.02 (2H, s), 3.58 (2H, broad), 3.18–2.28 (5H + DMSO, m), 2.11 (2H, t), 1.87–1.60 (6H, m), 1.52–1.18 (10H, m). (300MHz) |
| 12 (from 4-bromo-2-chloro-benzoic acid and 1-cyclohexane-boronic acid) | | 12.4 (2H, broad), 7.99–7.73 (2H, broad), 7.42–6.80 (2H, d), 7.32 (1H, pseudo-s), 7.18 (4H, dd), 7.06 (1H, d), 6.90 (1H, t), 5.07 (2H, s), 3.58 (2H, broad), 3.20–2.28 (5H + DMSO, m), 2.11 (2H, t), 1.88–1.61 (6H, m), 1.52–1.10 (10H, m). (200MHz) |

Ex. 13

4-{[(4-carboxybutyl)(2-{2-[(3-fluoro-4'-trifluoromethyl-1,1'-biphenyl-4-yl)methoxy]phenyl}ethyl)amino]methyl}benzoic acid hydrochloride

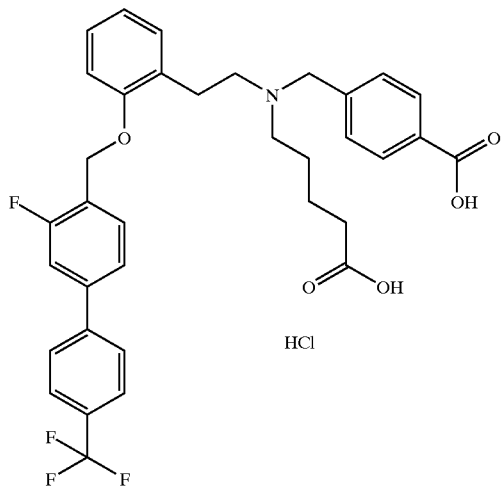

0.5 ml (2 mmol) of a 4-molar solution of HCl in dioxane is added to a solution of 220 mg of 4-{[(4-carboxybutyl)(2-{2-[(3-fluoro-4'-trifluoromethyl-1,1'-biphenyl4-yl)methoxy]phenyl}ethyl)amino]methyl}benzoic acid from Ex. 3 in 0.2 ml of dioxane, and the mixture is stirred at 60° C. for 1 h. The mixture is then concentrated by evaporation and the resulting colorless oil is triturated repeatedly with diethyl ether. The resulting crystals are filtered and dried.

$^1$H NMR: δ[ppm] (DMSO-$d_6$): 12.60 (2H, broad), 10.40 (1H, broad), 8.02–7.78 (6H, m), 7.76–7.54 (5H, m), 7.37–7.08 (3H, m), 6.93 (1H, t), 5.19 (2H, s), 4.40 (2H, s), 3.22–2.89 (6H, m), 2.14 (2H, t), 1.79–1.52 (2H, m), 1.50–1.29 (2H, m). (200 MHz) MS (ESI): 624 (M+H–HCl+).

What is claimed is:

1. A compound of the general formula (I)

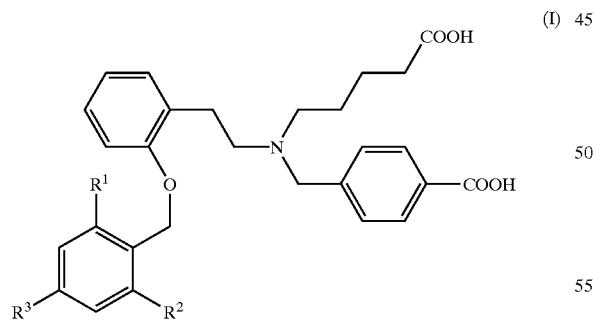

wherein
R$^1$ represents halogen;
R$^2$ represents H or halogen;
R$^3$ represents $C_{3-8}$-cycloalkyl, $C_{3-8}$-cycloalkenyl or phenyl, where the phenyl radical may additionally carry a substituent selected from the group consisting of halogen, $C_{1-6}$-alkyl, $C_{1-6}$-alkoxy, and CF$_3$;
or a pharmaceutically acceptable salts or stereoisomer thereof.

2. The compound of claim 1, characterized in that
R$^1$ represents F or Cl;
R$^2$ represents H;
R$^3$ represents $C_{3-8}$-cycloalkyl, $C_{3-8}$-cycloalkenyl or phenyl, where the phenyl radical may additionally carry a substituent selected from the group consisting of F, Cl, Br, methyl, ethyl, n-propyl, i-propyl, n-butyl, i-butyl, t-butyl, methoxy, ethoxy, n-propoxy, i-propoxy, n-butyloxy, i-butyloxy, t-butyloxy, and CF$_3$;
or a pharmaceutically acceptable salts or stereoisomer thereof.

3. The compound of claim 1, characterized in that
R$^1$ represents F or Cl;
R$^2$ represents H;
R$^3$ represents cyclohexyl, 1-cyclohexenyl or phenyl, where the phenyl radical may additionally carry a substituent from selected the group consisting of F, Cl, t-butyl, OMe, and CF$_3$;
or a pharmaceutically acceptable salt or stereoisomer thereof.

4. A process for preparing compounds of the general formula (I),

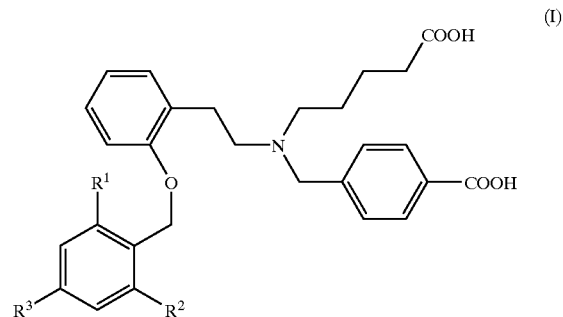

characterized in that compounds of the formula (II)

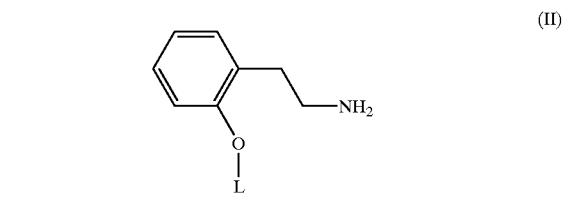

wherein
L represents methyl
is reacted with a $C_{1-6}$-alkyl 4-formylbenzoate in an organic solvent, if appropriate with heating and simultaneous or subsequent addition of a reducing agent, to give compounds of the formula (III)

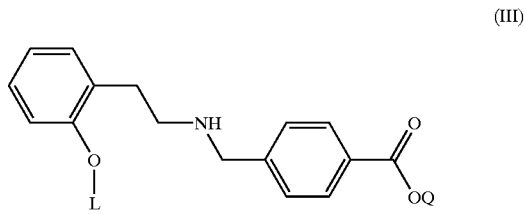

where

L is as defined above and Q represents a $C_{1-6}$-alkyl radical, then the ether group of the compound of formula (III) is cleaved to produce the free hydroxyl group, and the amino group of the compound of formula (III) is subsequently reacted with a $C_{1-6}$-alkyl ω-halovalerate in an organic solvent in the presence of a base with heating to give a compounds of the formula (IV)

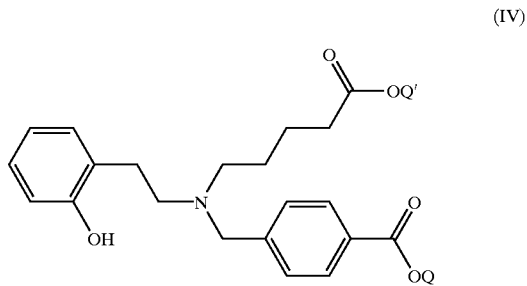

(IV)

wherein

Q is as defined above and Q' represents a $C_{1-6}$-alkyl radical, then the hydroxyl group of the compound of formula (IV) is reacted with a compound of the formula IV-A in an organic solvent in the presence of a base with heating

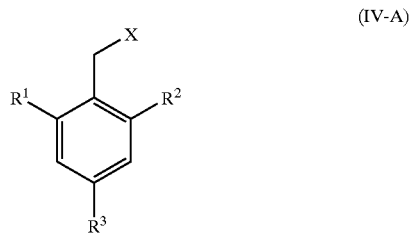

(IV-A)

wherein $R^1$ represents halogen;

$R^2$ represents H or halogen;

$R^3$ represents $C_{3-8}$-cycloalkyl, $C_{3-8}$-cycloalkenyl or phenyl, where the phenyl radical may additionally carry a substituent selected from the group consisting of halogen, $C_{1-6}$-alkyl, $C_{1-6}$alkoxy, and $CF_3$; and X' represents halogen to give compounds of the formula (V)

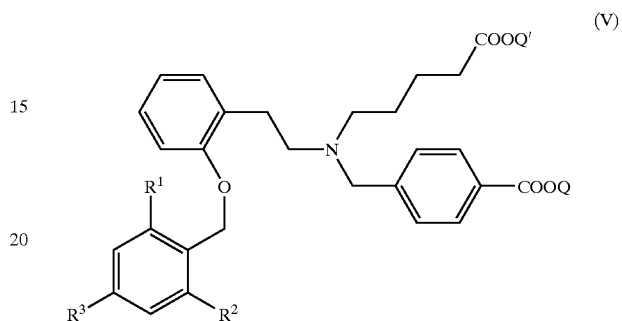

(V)

and the compounds of the formula (V) is then hydrolyzed under alkaline conditions to give the compounds of the formula (I).

5. A pharmaceutical composition, comprising at least one compound of the general formula (I) of claim 1, plus a pharmaceutically acceptable carrier.

6. A method for treating angina pectoris, or an ischemia, comprising administering to a subject in need thereof an effective amount of a compound of claim 1.

7. A method for treating hypertension, or arteriosclerosis comprising administering to a subject in need thereof an effective amount of a compound of claim 1.

8. A method for treating fibrosis of the liver comprising administering to a subject in need thereof an effective amount of a compound of claim 1.

* * * * *